United States Patent [19]

Lin

[11] Patent Number: 5,278,334
[45] Date of Patent: Jan. 11, 1994

[54] RACEMIZATION PROCESS

[75] Inventor: Ronny W. Lin, Baton Rouge, La.

[73] Assignee: Ethyl Corporation, Richmond, Va.

[21] Appl. No.: 955,217

[22] Filed: Oct. 1, 1992

[51] Int. Cl.$^5$ .................. C07C 69/76; C07C 51/10
[52] U.S. Cl. .................. 560/105; 560/231; 560/248; 562/401
[58] Field of Search .............. 562/401; 560/105, 231, 560/248

[56]  References Cited

U.S. PATENT DOCUMENTS

| | | | |
|---|---|---|---|
| 4,515,811 | 5/1985 | Holton | 562/401 |
| 4,723,033 | 2/1988 | Erickson | 562/401 |
| 4,724,102 | 2/1988 | Cannata et al. | 562/401 |

FOREIGN PATENT DOCUMENTS

| | | |
|---|---|---|
| 72040 | 2/1983 | European Pat. Off. |
| 3227543 | 9/1988 | Japan |
| 2-111741 | 4/1990 | Japan |

Primary Examiner—Paul J. Killos
Attorney, Agent, or Firm—Richard J. Hammond

[57] ABSTRACT

A method for racemizing an optically active aliphatic carboxylic acid, or ester thereof, of the formula:

$$R_4-\underset{R_2}{\underset{|}{\overset{R_3}{\overset{|}{C}}}}-\overset{O}{\overset{\|}{C}}-OR_1 \qquad I$$

where $R_1$ is hydrogen or $C_1$ to $C_6$ linear or branched alkyl; $R_2$, $R_3$ and $R_4$ are different and are hydrogen or $C_1$ to $C_6$ linear or branched alkyl, $C_1$ to $C_6$ linear or branched haloalkyl, aralkyl, cycloalkyl, alkyl substituted cycloalkyl, $C_6$ to $C_{10}$ aryl, $C_1$ to $C_6$ linear or branched alkoxy, $C_6$ to $C_{10}$ aryloxy, $C_1$ to $C_6$ alkylthio, $C_2$ to $C_8$ cycloalkylthio, $C_6$ to $C_{10}$ arylthio, $C_6$ to $C_{10}$ arylcarbonyl, $C_4$ to $C_8$ cycloalkenyl, trifluoromethyl, halo, $C_4$ to $C_5$ heteroaryl, $C_{10}$ to $C_{14}$ aryl, or biphenyl unsubstituted or substituted with methyl or halo, comprising heating said optically active carboxylic acid, ester or salt thereof at a temperature of from about 100° C. to about 400° C. at a hydrogen pressure of less than 40 atm in which palladium has a valence of 0-2 for a time sufficient to racemize said carboxylic acid, ester or salt thereof.

18 Claims, No Drawings

RACEMIZATION PROCESS

FIELD OF THE INVENTION

This invention relates to a process for converting an enantiomeric form of certain aliphatic carboxylic acids into a racemic mixture of enantiomers. This invention specifically relates to the racemization of one of the enantiomers of profen-type carboxylic acids or ester.

BACKGROUND OF THE INVENTION

Profen-types of compounds are typically defined as propionic acids (or esters) bearing at least one aromatic substituent, usually α- to the carboxylic function.

These carboxylic acids have an asymmetric carbon atom (the carbon atom adjacent to the carbonyl group) that typically produces a racemic mixture of these acids [a mixture of both the (+) and (−) or dextro and levo rotatory forms]. For example, ibuprofen [(2-(4-isobutylphenyl)propionic acid)], a commercially and pharmaceutically important chemical compound, is typically produced and sold as the racemic mixture. Many other of the pharmaceutically-active profen drugs are also produced as racemates and administered in this form. However, it is well known that the physiological utility of the racemic mixtures is almost exclusively focused on one enantiomer, the other having either no effect or even diminishing the effect of the active enantiomer. Thus the S(+) form of ibuprofen is physiologically active in reducing inflammation and in providing an analgesic effect See, for example, U.S. Pat. Nos. 4,851,444 and 4,877,620. The R(−) enantiomer is devoid of activity for these indications, although it is, in part, converted in vivo into the S(+) compound. Other profens, i.e., naproxen, are only prescribed as the single enantiomer.

OBJECTS OF THE INVENTION

It is an object of this invention to provide a process whereby the inactive or undesirable enantiomer of profen-type carboxylic acids may be converted into the other usable, desirable enantiomer.

It is a further object of this invention to carry out the conversion of one enantiomer of profen-type carboxylic acids into the other enantiomer in an efficient and economical manner.

These and other objects of the present invention are more completely described hereafter in the description of the preferred embodiment.

DESCRIPTION OF THE PREFERRED EMBODIMENTS

The process of the present invention involves using one of the enantiomeric forms (or an enantiomerically enriched mixture) of such carboxylic acids as a starting material and subjecting this starting material to the process of the present invention whereby conversion of one enantiomer to the other is effected. It should be noted, however, that the present conversion process only functions to achieve a racemic mixture of the enantiomers, i.e. it is a racemization process.

The process involves racemizing the enantiomer (or the mixture of enantiomers enriched in one enantiomeric form) in a hydrogen atmosphere at a temperature of from about 100° C. to about 400° C. Preferably, the process is carried out at about 150° C. to about 350° C., most preferably about 180° C. to about 300° C. The time of conversion to the racemic mixture is dramatically affected by adding to the aqueous solution a catalytically effective amount of a palladium compound having a valence of 0-2 for a time sufficient to racemize the carboxylic acid or ester. Typically, these times are from about 10 minutes to about 24 hours, especially 0.5 to 16 hours.

The carboxylic acids or salts or esters thereof useful in the process of the present invention have the formula:

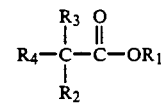

where $R_1$ is hydrogen or $C_1$ to $C_6$ linear or branched alkyl, $R_2$, $R_3$ and $R_4$ are different and are hydrogen or $C_1$ to $C_6$ linear or branched alkyl, e.g., methyl or ethyl; $C_1$ to $C_6$ linear or branched haloalkyl, e.g., chloromethyl, fluoromethyl, chloroethyl, fluoroethyl; aralkyl, e.g., benzyl; cycloalkyl, e.g., cyclopropyl, cyclobutyl, cyclopentyl, or cyclohexyl; alkyl substituted cycloalkyl, e.g., methylcyclohexyl; $C_6$ to $C_{10}$ aryl, e.g., phenyl unsubstituted or substituted with, for example, methyl, dimethyl, or butyl, especially isobutyl or phenyl substituted with $C_1$ to $C_4$ alkylthio, $C_1$ to $C_4$ alkoxy, cyano or halo, e.g., fluoro or chloro; $C_1$ to $C_6$ linear or branched alkoxy, e.g., methoxy, ethoxy, propoxy, or butoxy; $C_6$ to $C_{10}$ aryloxy, e.g., phenoxy or phenoxy substituted with, for example, methyl, dimethyl, butyl or isobutyl or phenoxy substituted with $C_1$ to $C_4$ alkylthio, $C_1$ to $C_4$ alkoxy, cyano or halo; $C_1$ to $C_6$ alkylthio, e.g., methylthio; $C_2$ to $C_8$ cycloalkylthio; $C_6$ to $C_{10}$ arylthio; $C_6$ to $C_{10}$ arylcarbonyl. e.g., benzoyl; $C_4$ to $C_8$ cycloalkenyl. e.g., cyclohexenyl; trifluoromethyl; halo, e.g., fluoro or chloro; $C_4$ to $C_5$ heteroaryl, e.g., furyl, pyrrolyl, or thienyl; or $C_{10}$ to $C_{14}$ aryl, e.g., naphthyl or naphthyl substituted with $C_1$ to $C_4$ alkyl, e.g., methyl, $C_1$ to $C_4$ alkoxy, e.g., ethoxy or halo; or biphenyl unsubstituted or substituted with methyl or halo, especially fluoro.

Preferred compounds of formula I are those of the formula:

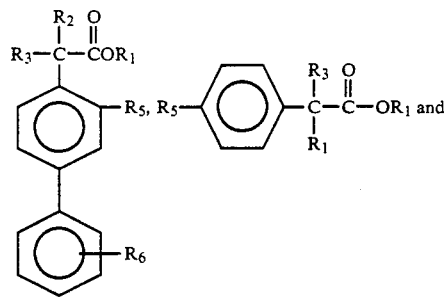

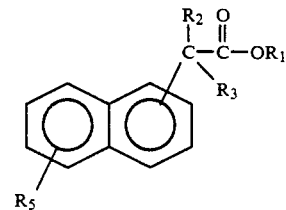

where $R_1$, $R_2$ and $R_3$ are as previously defined and $R_5$ and $R_6$ are $C_1$ to $C_4$ linear or branched alkyl, $C_1$ to $C_4$ linear or branched alkoxy or halo.

The racemization itself does not need $H_2$. But some hydrogen, at least initially, needs to be present to activate the catalyst. During the actual racemization, hydrogen is desirable in order to prevent the catalyst from deactivation. High hydrogen pressure is not favored since hydrogenation of the ring on the molecule could occur.

Accordingly, the partial pressure of hydrogen in the reaction vessel is at least about 1 atm at ambient temperature (or the temperature at which the vessel is charged). Any higher pressures of hydrogen can be used up to the pressure limits of the reaction apparatus subject to the reduction of the aromatic ring as noted above. A pressure up to about 3000 atm (about 30 MPa) is convenient in the process. More preferred is a pressure from about 200 to about 2000 atm (about 2 to about 20 MPa) at the reaction temperature, and most preferred is a pressure from about 550 to about 1350 atm (about 50 to about 14 MPa).

The racemization process of this invention is conducted in the presence of a reaction-promoting quantity of a palladium compound in which the palladium has a valence of 0-2.

The amount of palladium preferably employed is such as to provide from about 4 to about 8000 mols of aliphatic carboxylic acid, ester or salt thereof per mol of palladium; more preferred is an amount to provide from about 100 to about 4000 mols of said acid, ester or salt thereof per mol of palladium; the most preferred amount provides from about 200 to 2000 mols of said acid, ester of salt thereof per mol of palladium.

The presence of a solvent is not required in the process of this invention, although it may be desirable in some circumstances. Those solvents which can be used include one or more of the following: ketones, for example, acetone, methyl ethyl ketone, diethyl ketone, methyl-n-propyl ketone, acetophenone, and the like; linear, poly and cyclic ethers, for example, diethyl ether, di-n-propyl ether, di-n-butyl ether, ethyl-n-propyl ether, glyme (the dimethyl ether of ethylene glycol), diglyme (the dimethyl ether of diethylene glycol), tetrahydrofuran, dioxane, 1,3-dioxolane, and similar compounds; aromatic hydrocarbons, for example, toluene, ethyl benzene xylenes, and similar compounds and aliphatic hydrocarbons, for example, hexane, heptane, and similar compounds. Alcohols are also suitable as solvents, for example, methanol, ethanol, 1-propanol, 2-propanol, isomers of butanol, isomers of pentanol, etc. Acids and esters may also be used, such as formic or acetic acid or ethyl acetate, etc. When an ester or an alcohol is used as solvent, the product is either the corresponding ester of the corresponding free carboxylic acid or the mixed ester if $R_2$ is not the same as the alcohol solvent (if no water is present in the reaction) or a mixture of the ester and the free acid itself (if water is present).

Most highly preferred are racemization reactions that are solvent-free which advantageously cause minimal dilution and better recovery of the racemized product. When solvents are used, however, the amount can be up to about 100 mL per gram of aliphatic carboxylic acid, ester or salt thereof, but the process is most advantageously conducted in the presence of less than 20 mL per gram of said acid, ester or salt thereof.

By using the above disclosed palladium catalytic compound, the time period to achieve a racemic mixture is dramatically reduced depending on the ratio of enantiomers to catalyst and the reaction temperature. For example, a composition comprising 70% $R(-)$ enantiomer and 30% $S(+)$ enantiomer will achieve about 50:50 racemization in about 3 to about 4 hours at about 200° C. Of course, slower racemization will occur when the mixture approaches the 50:50 racemate.

As indicated above, the process of the present invention is useful for conversion of one of the enantiomeric forms of the disclosed aliphatic carboxylic acid into the other only up to the point of achieving a racemic mixture of enantiomers. The racemic mixture is, of course, useful as is or it may be subject to other processes to separate the enantiomeric mixture.

EXAMPLES

The following examples are illustrative of the process of the present invention.

EXAMPLE 1

An enriched mixture of ibuprofen having 84.3% of the $R(-)$enantiomer and 15.7% $S(+)$enantiomer: 75 g of (~2 wt %) ibuprofen in a hexane solution and 0.14 g of Pd (5 wt %)/C were charged into a 300 cc s.s. −316 autoclave. After purging the reactor with hydrogen, the mixture was heated from 25° C. at 0 psig with stirring to 190°-200° C. (at 200-240 psig) for 3 hours. No additional $H_2$ was added during the racemization. The pressure was mainly $C_6$ pressure. HPLC showed that the product had 61.5% R-ibuprofen and 38.5% S-ibuprofen.

EXAMPLE 2

97 g of the feed of Example 1 and 0.3 g of the Pd/C catalyst were used. After purging the reactor With hydrogen, the mixture was heated with stirring to 200° C. (at 230-240 psig) for 4 hours. The product had normalized composition of 53.4% R-ibuprofen and 46.6% S-ibuprofen.

I claim:

1. A method for racemizing an optically active aliphatic carboxylic acid, ester or salt thereof, of the formula:

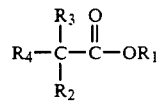

where $R_1$ is hydrogen or $C_1$ or $C_6$ linear or branched alkyl; $R_2$, $R_3$ and $R_4$ are different and are hydrogen or $C_1$ to $C_6$ linear or branched alkyl, $C_1$ to $C_6$ linear or branched haloalkyl, aralkyl, cycloalkyl, alkyl substituted cycloalkyl, $C_1$ to $C_6$ linear or branched alkoxy, $C_6$ to $C_{10}$ aryloxy, $C_1$ to $C_6$ alkylthio, $C_2$ to $C_8$ cycloalkylthio, $C_6$ to $C_{10}$ arylthio, $C_6$ to $C_{10}$ arylcarbonyl, $C_4$ to $C_8$ cycloalkenyl, trifluoromethyl, halo, $C_4$ to $C_5$ heteroaryl, $C_6$ to $C_{14}$ aryl, or biphenyl unsubstituted or substituted with methyl or halo, comprising heating a solution of said optically active carboxylic acid, ester or salt thereof at a temperature of from about 100° C. to about 400° C. and a hydrogen pressure of less than 40 atm in the presence of a catalytically effective quantity of palladium in which palladium has a valence of 0-2 for a time sufficient to racemize said carboxylic acid or ester thereof.

2. The method according to claim 1 wherein said temperature is from about 150° C. to about 350° C.

3. The method according to claim 1 wherein said temperature is from about 180° C. to about 300° C.

4. The method according to claim 1 wherein said aliphatic carboxylic acid thereof is a 2-arylpropionic acid derivative thereof.

5. The method according to claim 4 wherein said ester is a $C_1$ to $C_6$ linear or branched ester.

6. The method according to claim 1 wherein said heating is carried out over a period of from about 0.50 hour to about 16 hours.

7. The method according to claim 1 wherein said aliphatic carboxylic acid is 2-(6-methoxy-2-naphthyl)-propionic acid, 2-(4-isobutylphenyl)propionic acid or 2-(2-fluoro-4-biphenyl)propionic acid.

8. The method of claim 2 wherein said aliphatic carboxylic acid is 2-(4-isobutylphenyl) propionic acid.

9. The method according to claim 1 wherein the palladium compound is Pd(0).

10. A method for racemizing R(−)-ibuprofen comprising heating a solution of said ibuprofen at a temperature of from about 100° C. to about 400° C. at a hydrogen pressure of less than 40 atm in the presence of a catalytically effective amount of a palladium compound for a time sufficient to racemize said ibuprofen.

11. The method according to claim 10 wherein said temperature is from about 150° C. to about 350° C.

12. The method according to claim 10 wherein said temperature is from about 180° C. to about 300° C.

13. The method according to claim 10 wherein said aliphatic carboxylic acid thereof is a 2-arylpropionic acid derivative thereof.

14. The method according to claim 13 wherein said ester is a $C_1$ to $C_6$ linear or branched ester.

15. The method according to claim 10 wherein said heating is carried out over a period of from about 0.50 hour to about 16 hours.

16. The method according to claim 10 wherein said aliphatic carboxylic acid is 2-(6-methoxy-2-naphthyl)-propionic acid, 2-(4-isobutylphenyl)propionic acid or 2-(2-fluoro-4-biphenyl)propionic acid.

17. The method of claim 10 wherein said aliphatic carboxylic acid is 2-(4-isobutylphenyl) propionic acid.

18. The method according to claim 10 wherein the palladium compound is Pd(0).

* * * * *